(12) United States Patent
Tanaka

(10) Patent No.: US 8,389,742 B2
(45) Date of Patent: Mar. 5, 2013

(54) 3-HYDRAZINO-2,5-DIOXOPYRROLIDINE-3-CARBOXYLATE, PROCESS FOR PRODUCTION OF THE SAME, AND USE OF THE SAME

(75) Inventor: Daisuke Tanaka, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 20 days.

(21) Appl. No.: 13/093,202

(22) Filed: Apr. 25, 2011

(65) Prior Publication Data

US 2011/0201807 A1 Aug. 18, 2011

Related U.S. Application Data

(62) Division of application No. 12/309,101, filed as application No. PCT/JP2007/061887 on Jun. 13, 2007, now Pat. No. 8,003,808.

(30) Foreign Application Priority Data

Jul. 7, 2006 (JP) ................................. 2006-187588

(51) Int. Cl.
*C07D 207/30* (2006.01)
(52) U.S. Cl. ....................................................... 548/531
(58) Field of Classification Search .................... 548/531
See application file for complete search history.

(56) References Cited

U.S. PATENT DOCUMENTS 5,258,382 A 11/1993 Negoro et al.

FOREIGN PATENT DOCUMENTS

| JP | 5-186472 | 7/1993 |
| JP | 6-192222 | 7/1994 |

OTHER PUBLICATIONS

Negoro et al. (J. Med. Chem., 41 (1998), 4118-4129).*

International Search Report dated Jul. 31, 2007 in the International (PCT) Application PCT/JP2007/061887 of which the present application is the U.S. National Stage.
English translation of PCT Written Opinion dated Jan. 29, 2009 in the International (PCT) Application PCT/JP2007/061887 of which the present application is the U.S. National Stage.
Toshiyuki Negoro et al., "Novel, Highly Potent Aldose Reductase Inhibitors: (R)-(—)-2-(4-Bromo-2-fluorobenzyl)-1,2,3,4-tetrahydropyrrolo[1,2-a]pyrazine-4-spiro-3'-pyrrolidine-1,2',3,5'-tetrone (AS-3201) and Its Congeners", Journal of Medicinal Chemistry, vol. 41, pp. 4118-4129, 1998.
Mashiko et al., "En Route to an Efficient Catalytic Asymmetric Synthesis of AS-3201", J. Am. Chem. Soc. (2007) vol. 129, pp. 11342-11343.

* cited by examiner

*Primary Examiner* — Robert Havlin
(74) *Attorney, Agent, or Firm* — Wenderoth, Lind & Ponack, L.L.P.

(57) ABSTRACT

The present invention provides 3-hydrazino-2,5-dioxopyrrolidine-3-carboxylates of the formula (I):

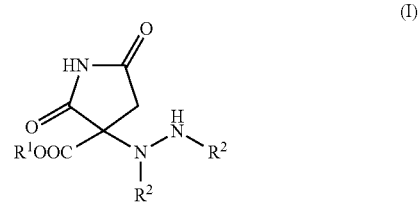

wherein $R^1$ is a $C_{1-6}$ alkyl group, etc., $R^2$ is a hydrogen atom or a $COOR^3$ group, wherein $R^3$ is a tert-$C_{4-6}$ alkyl group, a 2,2,2-trichloroethyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group, and a salt thereof, which are useful as a novel intermediate for preparing tetrahydropyrrolo[1,2-a]pyrazin-4-spiro-3'-pyrrolidine derivatives such as Ranirestat being promising therapeutic agents for diabetic complications in a short process and in an economically advantageous and safe manner, and the process for preparing the same.

20 Claims, No Drawings

3-HYDRAZINO-2,5-DIOXOPYRROLIDINE-3-CARBOXYLATE, PROCESS FOR PRODUCTION OF THE SAME, AND USE OF THE SAME

This application is a divisional application of Ser. No. 12/309,101, filed Jan.7, 2009, now U.S. Pat. No. 8,003,808 which is a 371 application of PCT/JP 2007/061887, filed Jun. 13, 2007.

TECHNICAL FIELD

This invention relates to a novel 3-hydrazino-2,5-dioxopyrrolidine-3-carboxylate useful as an intermediate of active pharmaceutical ingredient of a therapeutic agent for diabetic complications, etc., and a process for preparing the same, as well as a process for preparing Ranirestat being useful as a therapeutic agent for diabetic complications using the intermediate.

BACKGROUND ART

Tetrahydropyrrolo[1,2-a]pyrazin-4-spiro-3'-pyrrolidine derivatives which are promising therapeutic agents for diabetic complications showing a potent aldose reductase inhibitory activity are disclosed in the literature (for example, see JP-A-5-186472; and J. Med. Chem., 1998, 41, p. 4118 to 4129). Also Ranirestat [AS-3201; (3R)-2'-(4-bromo-2-fluorobenzyl)spiro[pyrrolidin-3,4'(1'H)-pyrrolo[1,2-a]pyrazine]-1',2,3',5(2H')-tetraone] selected among these derivatives has been developed clinically. 3-Amino-2,5-dioxopyrrolidine-3-carboxylates are disclosed as the intermediate suitable to prepare these derivatives on the industrial scale in the literature (for example, see JP-A-6-192222), and the process for preparing the same is also disclosed in the literatures (for example, JP-A-5-186472, JP-A-6-192222 and J. Med. Chem., 1998, 41, p. 4118 to 4129 as aforementioned). The summary of the process for preparing the same is illustrated in following Scheme 1.

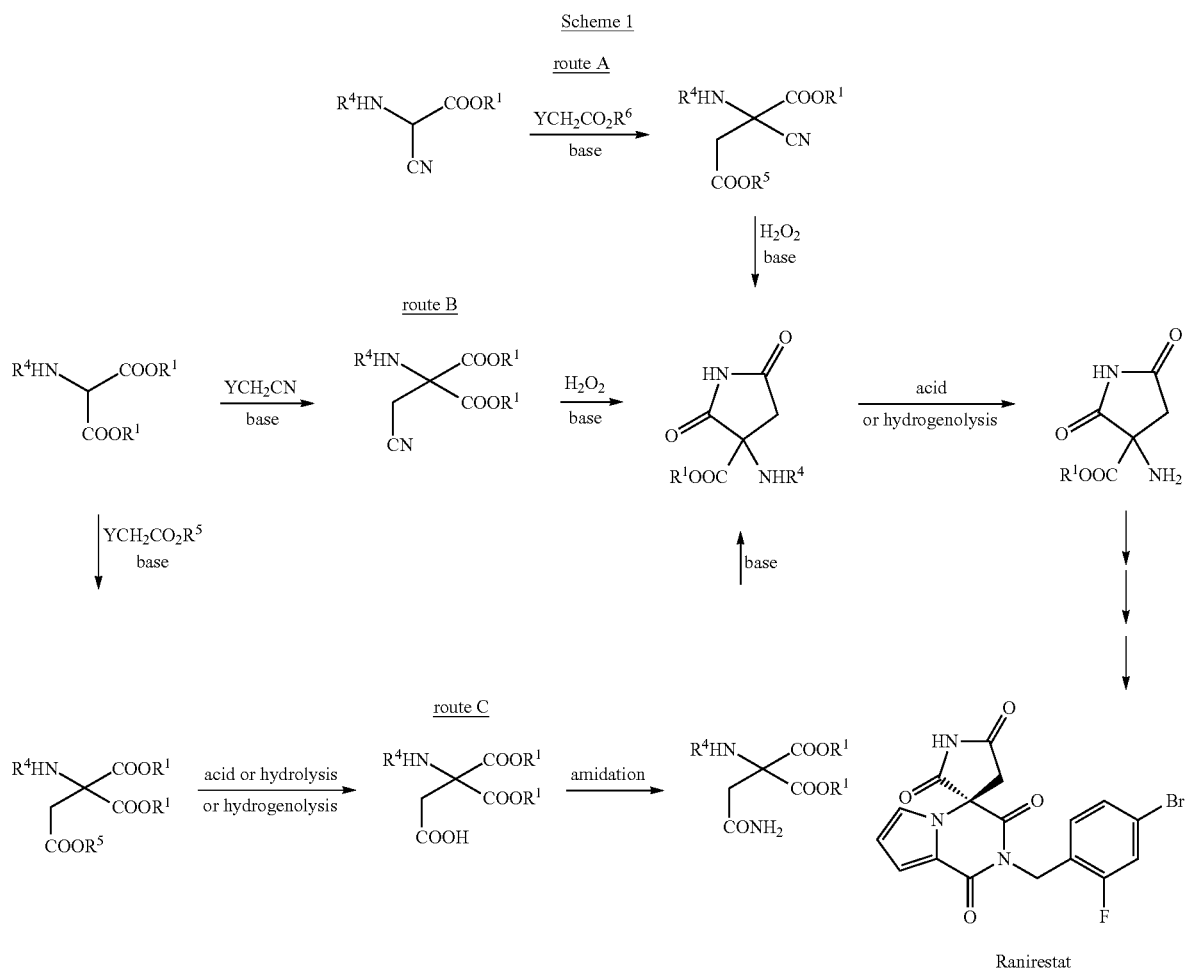

wherein $R^1$ and $R^6$ are a protecting group for a carboxyl group, $R^4$ is a group cleavable by hydrogenolysis or a tert-butoxycarbonyl group, $R^5$ is a tert-butyl group or a group cleavable by hydrolysis or hydrogenolysis.

In the above route A and route B, there is a step for a ring closure reaction of the 3-cyanopropionic acid ester moiety using hydrogen peroxide and base to form 2,5-dioxopyrrolidine ring and then it is difficult for this step to control the reaction temperature. This is caused by the fact that this step is an exothermic reaction and thus often happens to foam violently. Therefore it is necessary to proceed with this step while cooling. But excess cooling makes the progress of the reaction insufficient to complete and results in lowering the yield and the purity of the desired product. On the other hand, insufficient cooling results in forming a large amount of side products and thus similarly as above, results in lowering the yield and the purity of the desired product. Therefore it is necessary to improve this step. Also relatively high level of hydrogen peroxide used in this step is dangerous and thus there is a risk of decomposing violently in the reaction. Therefore it is also desirous of a method for avoiding the use thereof.

The route C is the process without use of hydrogen peroxide. But it is desirous of a more economically advantageous method since this route requires a large number of steps in total compared to the route A and the process shown in Scheme 2 mentioned below.

A literature describes a preparation of 2-benzyloxycarbonylamino-2-ethoxycarbonylsuccinimide by reacting diethyl benzyloxycarbonylaminomalonate with sodium hydride and bromoacetamide in the examples (see JP-A-6-192222). But this process is not preferred for the industrial scale preparation because of low yield (36.5%) as well as evolution of hydrogen gas in the course of the reaction with sodium hydride.

DISCLOSURE OF INVENTION

Problems to be Solved by Invention

An object of the present invention is to provide a process for preparing active pharmaceutical ingredient of tetrahydropyrrolo[1,2-a]pyrazin-4-spiro-3'-pyrrolidine derivatives (for example, Ranirestat) which are promising therapeutic agents for diabetic complications in a short process and in an economically advantageous and safe manner. Specifically, an object of the present invention is to provide a process for preparing 3-amino-2,5-dioxopyrrolidine-3-carboxylates as an intermediate useful for active pharmaceutical ingredient without use of hydrogen peroxide and in a short process and in an economically advantageous manner.

Means for Solving Problem

The present inventor has intensively studied in order to achieve the above-mentioned objects, and has found that 3-hydrazino-2,5-dioxopyrrolidine-3-carboxylates can be prepared from 2,5-dioxopyrrolidine-3-carboxylates in one step, conveniently and in high yields, and further the 3-hydrazino-2,5-dioxopyrrolidine-3-carboxylates can be converted into 3-amino-2,5-dioxopyrrolidine-3-carboxylates in one or two steps, conveniently and in high yields, and has accomplished the present invention. That is, the present invention provides novel 3-hydrazino-2,5-dioxopyrrolidine-3-carboxylates and salts thereof (hereinafter abbreviated as the compound of the invention) useful as an intermediate for tetrahydropyrrolo[1,2-a]pyrazin-4-spiro-3'-pyrrolidine derivatives, etc.

That is, the present invention relates to the following embodiments:

[1] 3-Hydrazino-2,5-dioxopyrrolidine-3-carboxylates of the formula (I):

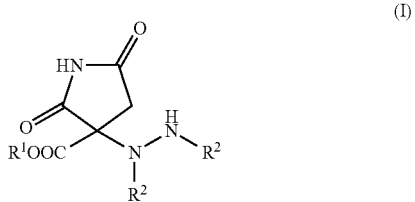

(I)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group; or an aryl group or a heteroaryl group optionally substituted by one or two groups independently selected from the group consisting of a $C_{1-4}$ alkyl group and a $C_{1-4}$ alkoxy group;

$R^2$ is a hydrogen atom or a $COOR^3$ group;

wherein when $R^1$ is a $C_{1-6}$ alkyl group other than a tert-$C_{4-6}$ alkyl group; a $C_{3-8}$ cycloalkyl group; or an aryl group or a heteroaryl group optionally substituted by one or two groups independently selected from the group consisting of a $C_{1-4}$ alkyl group and a $C_{1-4}$ alkoxy group, then $R^3$ is a tert-$C_{4-6}$ alkyl group; a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group;

when $R^1$ is a tert-$C_{4-6}$ alkyl group, then $R^3$ is a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group;

when $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group, then $R^3$ is a tert-$C_{4-6}$ alkyl group or a 2,2,2-trichloroethyl group, or a salt thereof.

[2] The 3-hydrazino-2,5-dioxopyrrolidine-3-carboxylates as set forth in [1] wherein $R^1$ is a $C_{1-6}$ alkyl group other than a tert-$C_{4-6}$ alkyl group, $R^2$ is a hydrogen atom or a $COOR^3$ group, and $R^3$ is a tert-$C_{4-6}$ alkyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group, or a salt thereof.

[3] The 3-hydrazino-2,5-dioxopyrrolidine-3-carboxylates as set forth in [1] wherein $R^1$ is a methyl group, an ethyl group, a propyl group or an isopropyl group, and $R^2$ is a hydrogen atom, a tert-butoxycarbonyl group or a benzyloxycarbonyl group, or a salt thereof.

[4] The 3-hydrazino-2,5-dioxopyrrolidine-3-carboxylates as set forth in [1] selected from the group consisting of
ethyl 3-[N,N'-bis(benzyloxycarbonyl)hydrazino]-2,5-dioxopyrrolidine-3-carboxylate,
ethyl 3-[N,N'-bis(tert-butoxycarbonyl)hydrazino]-2,5-dioxopyrrolidine-3-carboxylate, and
ethyl 3-hydrazino-2,5-dioxopyrrolidine-3-carboxylate monohydrochloride,
or a salt thereof.

The present invention provides the process for preparing the novel 3-hydrazino-2,5-dioxopyrrolidine-3-carboxylates as follows:

[5] A process for preparing
3-hydrazino-2,5-dioxopyrrolidine-3-carboxylates of the formula (Ia):

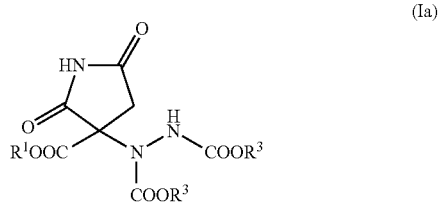

(Ia)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group; or an aryl group or a heteroaryl group optionally substituted by one or two groups independently selected from the group consisting of a $C_{1-4}$ alkyl group and a $C_{1-4}$ alkoxy group;

wherein when $R^1$ is a $C_{1-6}$ alkyl group other than a tert-$C_{4-6}$ alkyl group; a $C_{3-8}$ cycloalkyl group; or an aryl group or a heteroaryl group optionally substituted by one or two groups independently selected from the group consisting of a $C_{1-4}$ alkyl group and a $C_{1-4}$ alkoxy group, then $R^3$ is a tert-$C_{4-6}$ alkyl group; a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group;

when $R^1$ is a tert-$C_{4-6}$ alkyl group, then $R^3$ is a 2,2,2-trichloroethyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group;

when $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group, then $R^3$ is a tert-$C_{4-6}$ alkyl group or a 2,2,2-trichloroethyl group, comprising the step of adding the compound of the formula (III):

wherein $R^3$ is as defined above, to the compound of the formula (II):

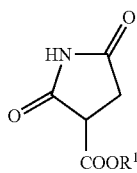

wherein $R^1$ is as defined above.

[6] A process for preparing 3-hydrazino-2,5-dioxopyrrolidine-3-carboxylates of the formula (Ib):

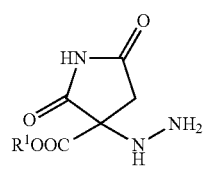

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group; or an aryl group or a heteroaryl group optionally substituted by one or two groups independently selected from the group consisting of a $C_{1-4}$ alkyl group and a $C_{1-4}$ alkoxy group, comprising the following steps:
(1) a step of undergoing a hydrogenolysis of the compound of the formula (Ia) as set forth in [5] wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group in the presence of a palladium catalyst;
(2) a step of reacting the compound of the formula (Ia) as set forth in [5] wherein $R^3$ is a tert-$C_{4-6}$ alkyl group with an acid; or
(3) a step of reacting the compound of the formula (Ia) as set forth in [5] wherein $R^3$ is a 2,2,2-trichloroethyl group with zinc.

The present invention provides the novel process for preparing the 3-hydrazino-2,5-dioxopyrrolidine-3-carboxylates using the compound of the formula (I) as a starting material as follows:

[7] A process for preparing the compound of the formula (IV):

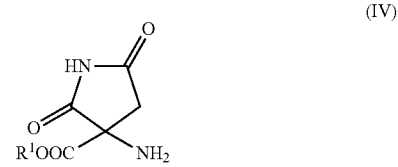

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group; or an aryl group or a heteroaryl group optionally substituted by one or two groups independently selected from the group consisting of a $C_{1-4}$ alkyl group and a $C_{1-4}$ alkoxy group, by using the formula (Ic):

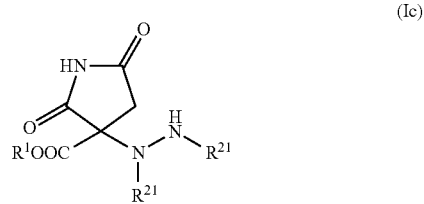

wherein $R^1$ is as defined above; and $R^{21}$ is a hydrogen atom or a $COOR^{31}$ group;

wherein $R^{31}$ is a 2,2,2-trichloroethyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group, comprising the following step:
a step of reacting the compound of the formula (Ic) wherein $R^{21}$ is a hydrogen atom or a $COOR^{31}$ group, wherein $R^{31}$ is a 2,2,2-trichloroethyl group with zinc; or
a step of undergoing a hydrogenolysis of the compound of the formula (Ic) wherein $R^{21}$ is a hydrogen atom or a $COOR^{31}$ group, wherein $R^{31}$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group (with the proviso that except the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group).

[8] The present invention provides a novel process for preparing 2'-(4-bromo-2-fluorobenzyl)spiro[pyrrolidine-3,4'(1'H)-pyrrolo[1,2-a]pyrazine]-1',2,3',5(2H')-tetraone, comprising the step of preparing the compound of the formula (I) as set forth in [1] by the process as set forth in [5] or [6], and the step of converting the compound of the formula (I) into 2'-(4-bromo-2-fluorobenzyl)spiro-[pyrrolidine-3,4(1'H)-pyrrolo[1,2-a]pyrazin e]-1',2,3 ',5(2H')-tetraone.

[9] The present invention provides the use of the compound of the formula (I) as set forth in [1] in the manufacture of 2'-(4-bromo-2-fluorobenzyl)spiro[pyrrolidine-3,4'(1'H)-pyrrolo[1,2-a]pyrazine ]-1',2,3',5(2H')-tetraone.

[10] A use of 3-hydrazino-2,5-dioxopyrrolidine-3-carboxylates as set forth in any one of [1] to [4] or a salt thereof in the manufacture of a medicament.

[11] The use of 3-hydrazino-2,5-dioxopyrrolidine-3-carboxylates as set forth in any one of [1] to [4] or a salt thereof in the manufacture of (3R)-2'-(4-bromo-2-fluorobenzyl)spiro[pyrrolidine-3,4'(1'H)-pyrrolo[1,2-a]pyr azine]-1',2,3',5(2H')-tetraone.

The present invention provides the novel process for preparing the (3R)-2'-(4-bromo-2-fluorobenzyl)spiro[pyrrolidine-3,4'(1'H)-pyrrolo[1,2-a]pyr azine]-1',2,3',5(2H')-tetraone as follows:

[12] A process for preparing (3R)-2'-(4-bromo-2-fluorobenzyl)spiro[pyrrolidine-3,4'(1'H)-pyrrolo[1,2-a]pyr azine]-1',2,3',5(2H')-tetraone, comprising using 3-hydrazino-2,5-dioxopyrrolidine-3-carboxylates as set forth in any one of [1] to [4] or a salt thereof as an intermediate or a starting material.

S[13] The process as set forth in [12], characterized by preparing 3-hydrazino-2,5-dioxopyrrolidine-3-carboxylates as set forth in any one of [1] to [4] or a salt thereof by the process as set forth in [5] or [6].

[14] A process for preparing (3R)-2'-(4-bromo-2-fluorobenzyl)spiro[pyrrolidine-3,4'(1H')-pyrrolo[1,2-a]pyr azine]-1',2,3',5(2H')-tetraone, comprising a step of preparing the compound of the formula (IV) as set forth in [7] and the step of converting the compound of the formula (IV) prepared in preceding step into (3R)-2'-(4-bromo-2-fluorobenzyl)spiro[pyrrolidine-3,4'(1'H)-pyrrolo[1,2-a]pyr azine]-1',2,3',5(2H')-tetraone.

[15] A process for preparing (3R)-2'-(4-bromo-2-fluorobenzyl)spiro[pyrrolidine-3,4'(1'H)-pyrrolo[1,2-a]pyr azine]-1',2,3',5(2H')-tetraone, comprising the following steps:

(1) a step of preparing the compound of the formula (IV) as set forth in [7];

(2) a step of performing an optical resolution of the compound of the formula (IV) prepared in the above step (1);

(3) a step of converting an amino group of the optically active compound prepared in the above step (2) (wherein the absolute configuration at carbon atom on 3 position of the dioxopyrrolidine ring of said compound is R) into 1-pyrrolyl group;

(4) a step of converting the pyrrolyl group of the product of the above step (3) into 2-trichloroacetylpyrrol-1-yl group; and (5) a step of reacting the product of the above step (4) with 4-bromo-2-fluorobenzylamine to convert it into (3R)-2'-(4-bromo-2-fluorobenzyl)spiro[pyrrolidine-3,4'(1'H)-pyrrolo[1,2-a]pyr azine]-1',2,3',5(2H')-tetraone.

Effect of the Invention

The compound of the present invention and the process for preparing the same can be used to prepare 3-amino-2,5-dioxopyrrolidine-3-carboxylates being useful as active pharmaceutical ingredient and an intermediate for preparing Ranirestat, etc., which are promising therapeutic agents for diabetic complications in a short process and in a safe and efficient manner.

BEST MODES FOR CARRYING OUT THE INVENTION

The present invention is explained in more detail below.

The salt of the compound represented by the formula (I) includes the salt of the compound of the formula (I) having the acidity or basicity sufficient to form a salt, for example, a salt with an alkali metal or an alkaline earth metal such as sodium, potassium or calcium, etc.; a salt with an organic base such as pyridine, triethylamine, diisopropylamine, dicyclohexylamine, etc.; a salt with amino acid such as lysine, arginine, glutamic acid or aspartic acid, etc.; a salt with inorganic acid such as hydrochloric acid, hydrobromic acid, hydroiodic acid, sulfuric acid or phosphoric acid, etc.; or a salt with an organic acid such as oxalic acid, malonic acid, maleic acid, fumaric acid, lactic acid, malic acid, citric acid, tartaric acid, trifluoroacetic acid, methanesulfonic acid, p-toluenesulfonic acid or trifluoromethanesulfonic acid, etc.

The compound of the formula (I) and a salt thereof may exist in a hydrate and/or a solvate form, thus these hydrates and/or solvates are also included in the compound of the invention. Also the compound of the formula (I) has one more than asymmetric carbon atom, thus it can exist in several stereoisomer forms. These stereoisomers and a mixture and a racemate thereof are also included in the compound of the invention.

The terms used herein are explained as follows. Unless defined otherwise, the definition for each group shall also be applied to where said group is a part of another group.

The "$C_{1-6}$alkyl group" is a straight chain or branched chain alkyl group having 1 to 6 carbon atoms, specifically such as methyl group, ethyl group, propyl group, isopropyl group, butyl group, isobutyl group, tert-butyl group, pentyl group, isopentyl group, neopentyl group and hexyl group, etc.

The "tert-$C_{4-6}$alkyl group" is a tert-butyl group optionally substituted by one to two methyl groups or one ethyl group, specifically such as tert-butyl group and tert-pentyl group, etc.

The specific example of "$C_{1-4}$ alkyl group" includes, for example, methyl group, ethyl group, propyl group, isopropyl group, n-butyl group, isobutyl group and tert-butyl group, etc.

The "$C_{3-8}$ cycloalkyl group" is a cyclic alkyl group having 3 to 8 carbon atoms, specifically such as cyclopropyl group, cyclobutyl group, cyclopentyl group and cyclohexyl group, etc.

The "$C_{1-4}$ alkoxy group" may be a straight chain or branched chain, specifically such as methoxy group, ethoxy group, propoxy group, isopropoxy group, butoxy group, isobutoxy group, sec-butoxy group and tert-butoxy group, etc.

The "aryl group" includes a fused polycyclic aromatic hydrocarbon group containing phenyl group or benzene ring, specifically such as phenyl group and naphthyl group, etc., and preferred specific example includes phenyl group.

The "heteroaryl group" includes a heteroaryl group in which 1 to 4 carbon atoms on a 5- to 6-membered monocyclic unsaturated hydrocarbon group or a polycyclic unsaturated hydrocarbon group fused thereto are replaced by heteroatom selected from the group consisting of N, O and S atoms, specifically such as pyridyl group, furyl group and thienyl group, etc.

A specific example of the "benzyl group in which the benzene ring moiety may be optionally substituted by a halogen atom, a $C_{1-4}$ alkyl group, a $C_{1-4}$ alkoxy group, a cyano group or a nitro group" includes, for example, benzyl group, 4-chlorobenzyl group, 3-bromobenzyl group, 4-methylbenzyl group, 3-methylbenzyl group, 2-methoxybenzyl group, 4-methoxybenzyl group, 4-cyanobenzyl group and 4-nitrobenzyl group, etc.

The "halogen atom" is fluorine atom, chlorine atom, bromine atom and iodine atom.

A specific example of "acid" includes, for example, an inorganic acid such as hydrogen chloride, hydrogen bromide, hydrogen iodide and sulfuric acid, etc., or an organic acid such as trifluoroacetic acid, methanesulfonic acid and trifluoromethanesulfonic acid, etc., preferably hydrogen chloride and trifluoroacetic acid.

The process for preparing the compound of the invention is explained as follows:

The compound of the formula (I) [the compound of the formula (Ia) and the compound of the formula (Ib) in Scheme 3] can be prepared by combining the type of a protecting group for a carboxyl group on 2,5-dioxopyrrolidine ring with the type of a protecting group for a carboxyl group on a hydrazino group appropriately and for example, according to the step A and step B illustrated in following Scheme 3.

Specific examples of the solvent used in the step A include methanol, ethanol, isopropanol, tert-butanol, ethyl acetate, acetonitrile, tetrahydrofuran, N,N-dimethylformamide, dimethylsulfoxide and water, etc., which can be used alone respectively or in a combination of two or more kinds thereof. The base is not necessarily required in the step A, but a use of the base can proceed with the reaction more efficiently. Specific examples of the base include potassium carbonate, sodium carbonate, sodium bicarbonate, triethylamine, pyridine, 1,8-diazabicyclo[5.4.0]undeca-7-ene, sodium ethoxide and potassium tert-butoxide, etc. The amount used of the base is not limited otherwise, but can be selected from a catalytic amount to an excess amount to those of the compound of the formula (II). The reaction temperature is usually at 0 to 100° C., preferably 10 to 30° C.

The compound of the formula (II) can be prepared by reacting a diethyl malonate with 2-chloroacetamide in the presence of the base in one step according to a method described in JP-A-60-16989 or a similar method thereto.

The compound of the formula (III) is either commercially available, or can be prepared by a method that is well-known (or disclosed) in literatures or a similar method thereto.

The compound of the formula (Ib) (the compound wherein $R^2$ is a hydrogen atom in the formula (I)) can be prepared from the compound of the formula (Ia) by the following three methods (step B).

The first process for step B includes a method of reacting the compound of the formula (Ia) (with the proviso that except the compound wherein $R^1$ is tert-$C_{4-6}$ alkyl group) with an acid in an appropriate solvent. Specific examples of the solvent used in the reaction include ethyl acetate, dichloromethane, 1,4-dioxane, acetic acid and water, etc., which can be used alone respectively or in a combination of two or more kinds thereof. Specific examples of the acid used in the reaction include hydrogen chloride, hydrogen bromide, hydrogen iodide, sulfuric acid, trifluoroacetic acid, methane-

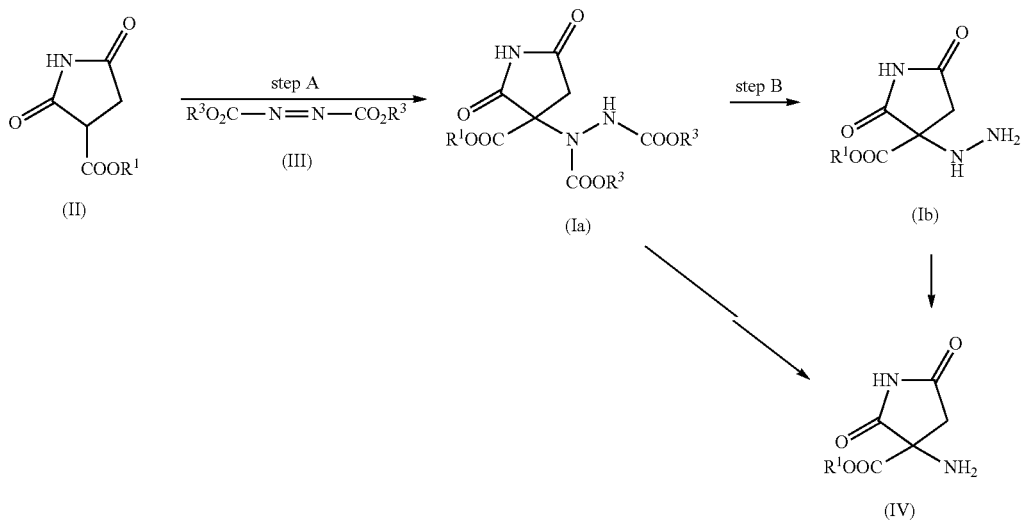

Scheme 3 wherein $R^1$ and $R^3$ are as defined above.

The compound of the formula (Ia) (the compound wherein $R^2$ is a $COOR^3$ group in the formula (I)) can be prepared by reacting the compound of the formula (II) with the compound of the formula (III) in an appropriate solvent in the presence or absence of a base (step A).

sulfonic acid and trifluoromethanesulfonic acid, etc., with among them hydrogen chloride or trifluoroacetic acid being preferred. A preferred reaction temperature is at 0 to 30° C.

The second process for step B includes a method of reacting the compound of the formula (Ia) wherein $R^3$ is 2,2,2-trichloroethyl group with zinc in an appropriate solvent. This process can be carried out according to the method described in Synthesis, 457 (1976) or a similar method thereto. Specific examples of the solvent include acetic acid, tetrahydrofuran and water, etc., which can be used alone respectively or in a combination of two or more kinds thereof. Zinc is usually used in an excess amount. The reaction temperature is usually at 10 to 120° C.

The third process for step 13 includes a method of undergoing a hydrogenolysis of the compound of the formula (Ia) wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group in an appropriate solvent in the presence of a catalyst such as palladium carbon ethylenediamine complex for a short duration. Specific examples of the solvent include ethyl acetate, methanol, ethanol, isopropanol and tetrahydrofuran, etc., which can be used alone respectively or in a combination of two or more kinds thereof. A preferred solvent is ethanol. The reaction temperature is usually at 0 to 80° C. The preferable reaction time is usually 1 to 4 hours at room temperature, but which depends on the kind of catalyst, a reaction temperature or a manner for stirring, etc.

The compound of the formula (Ic) [the compound of the formula (Ia) or the compound of the formula (Ib) wherein $R^{31}$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group and a nitro group) (with the proviso that except the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group)] is decomposed in a catalytic hydrogenolysis or a catalytic hydrogen transfer to produce the above compound of the formula (IV). The catalytic hydrogenolysis is carried out in an appropriate solvent under hydrogen at atmospheric pressure or increased pressure in the presence of a catalyst such as palladium-carbon, platinum-carbon, platinum oxide and Raney nickel, etc. Specific examples of the solvent include methanol, ethanol, isopropanol, acetic acid and water, etc., which can be used alone respectively or a combination of two or more kinds thereof. When a neutral solvent is used in the catalytic hydrogenolysis, an acid such as hydrogen chloride or trifluoroacetic acid, etc., may be added. The reaction temperature is usually at 0 to 80° C. The decomposition by catalytic hydrogen transfer can be carried out according to the method described in J. Heterocyclic Chem. 18, 31 (1981) and Indian J. Chem. 42B, 1774 (2003) or a similar method thereto. The source of hydrogen used includes, for example, ammonium formate, formic acid, cyclohexene and hydrazine, etc. Specific examples of the solvent include methanol, ethanol, isopropanol, acetic acid and water, etc., which can be used alone respectively or in a combination of two or more kinds thereof.

The above compound of the formula (Ic) [wherein $R^{31}$ is 2,2,2-trichloroethyl group] and the compound of the formula (Ib) can be reacted with zinc in an appropriate solvent according to the method described in Tetrahedron Lett. 30, 2889 (1989) to give the above compound of the formula (IV).

The compound of the formula (I) other than the compound of the formula (Ic) can be used in the preparation of the compound of the formula (Ib).

The compound of the formula (V) [for example, the optical active substance of the compound of the formula (IV) wherein $R^1$ is an ethyl group (the compound of Example 10 mentioned below)] which can be prepared from the compound of the formula (I) of the present invention is an intermediate of tetrahydropyrrolo[1,2-a]pyrazin-4-spiro-3'-pyrrolidine derivatives (for example, Ranirestat) which are promising therapeutic agents for diabetic complications described in aforementioned JP-A-5-186472 and JP-A-6-192222. Thus the compound of the formula (I) of the present invention is applicable as starting material of Ranirestat. Also JP-A-08-176105 describes that 2-ethoxycarbonyl-2-(2-trichloroacetylpyrrol-1-yl)succinimide, which can be prepared from the compound of the formula (IV) as a starting material, is an intermediate of 2-carboxysuccinimide derivatives useful as a therapeutic agent for diabetic complications. The compound of the invention having a chemically modifiable side chain can become an intermediate or a starting material useful in creating pharmaceuticals, since the 2,5-dioxopyrrolidine skeleton is a chemical structure often found in the substructure of compounds useful as pharmaceuticals such as a therapeutic agent for diabetes-related conditions or a central nervous system agents.

EXAMPLES

The present invention is illustrated in more detail below by Examples, but the present invention should not be construed to be limited thereto. The compounds were characterized by proton nuclear magnetic resonance spectrum ($^1$H NMR), carbon 13 nuclear magnetic resonance spectrum ($^{13}$C NMR), and mass spectrum (MS) analyses. Tetramethyl silane is used as an internal standard in the nuclear magnetic resonance spectrum analyses. Silica gel was used as a loading material for a flash column chromatography. For the abbreviations in Examples, Ph is phenyl group and Bu$^t$ is tert-butyl group.

Example 1

Preparation of Ethyl 3-[N,N'-bis(benzyloxycarbonyl) hydrazino]-2,5-dioxopyrrolidine-3-carboxylate

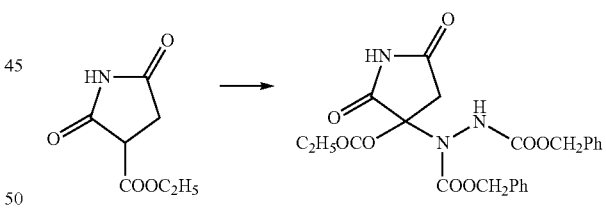

To a solution of 20% sodium ethoxide-ethanol solution (34.0 g) diluted with ethanol (40 ml) was added a solution of diethyl malonate (16.0 g) in ethanol (40 ml) dropwise over 30 minutes in ice-cooling. After stirring in ice-cooling for additional 30 minutes, thereto was added 2-chloroacetamide (4.7 g) in one portion and the mixture was stirred in ice-cooling for 30 minutes and then at room temperature for 20 hours. The white solid precipitated was collected by filtering and washed with a small amount of ethanol. This white solid was dissolved in water (300 ml) and this resulting aqueous solution was acidified with conc. hydrochloric acid and extracted with dichloromethane (50 ml) three times. The extract was dried over magnesium sulfate, filtered and concentrated to give a yellow oil. This was purified by a flash column chromatography (n-hexane:ethyl acetate=2:1→1:1) to give ethyl 2,5-dioxopyrrolidine-3-carboxylate (5.63 g, 66%).

$^1$H NMR (300 MHz, CDCl$_3$, 23° C.) δ: 4.28 (2H, q, J=7.4 Hz), 3.85 (1H, dd, J=5.0, 9.5 Hz), 3.15 (1H, dd, J=5.0, 18.5 Hz), 2.95 (1H, dd, J=9.3, 18.5 Hz), 1.32 (3H, t, J=7.1 Hz). $^{13}$C NMR (75 MHz, CDCl$_3$, 24° C.) δ: 175.9, 172.7, 167.2, 62.7, 47.7, 33.3, 14.0.

To a solution of ethyl 2,5-dioxopyrrolidine-3-carboxylate (3.92 g) in ethyl acetate (60 ml) was added dibenzyl azodicarboxylate (7.27 g), followed by potassium carbonate (317 mg) at room temperature. After this mixture was stirred at room temperature for 1 hour, the mixture was filtered through a Celite pad. The filtrate was concentrated and the resulting residue was purified by a flash column chromatography (hexane:ethyl acetate=2:1) to give the desired product (10.1 g, 94%) as amorphous.

$^1$H NMR (300 MHz, DMSO-d$_6$, 120° C.) δ: 11.4 (1H, br), 9.66 (1H, br), 7.35-7.25 (10H, m), 5.15-5.02 (4H, m), 4.14 (2H, q, J=7.1 Hz), 3.40 (1H, d, J=18.3 Hz), 3.17 (1H, d, J=18.2 Hz), 1.14 (3H, t, J=7.1 Hz).

Example 2

Preparation of ethyl 3-amino-2,5-dioxopyrrolidine-3-carboxylate

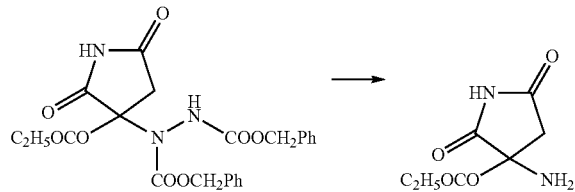

To a solution of the compound of Example 1 (496 mg) in acetic acid (15 ml) was added platinum oxide (102 mg). This mixture was stirred vigorously at 50° C. under hydrogen (atmospheric pressure) for 6 hours. During this reaction, to remove carbon dioxide generated with the progress of the reaction, the gas in the reactor was replaced with hydrogen gas several times. The reaction mixture was filtered through a Celite pad and then the Celite was washed with a small amount of acetic acid. The filtrate combined with the washers was concentrated and to the resulting residue was added toluene to remove azeotropically the residual acetic acid and then the mixture was concentrated again. To the residue was added ethyl acetate and the insoluble material was filtered off, and then the ethyl acetate solution was concentrated to give a crude product which was then purified by a flash column chromatography (chloroform:methanol=30:1) to give the desired product (126 mg, 64%) as crystal. $^1$H NMR (CDCl$_3$) data of this product were consistent with those of an optical active substance described in J. Med. Chem., 1998, 41, p. 4118 to 4129.

$^1$H NMR (400 MHz, CDCl$_3$, 22° C.) δ: 4.28 (2H, q, J=7.1 Hz), 3.18 (1H, d, J=18.0 Hz), 2.76 (1H, d, J=18.0 Hz), 1.29 (3H, t, J=7.2 Hz). $^1$H NMR (400 MHz, THF-d$_8$, 23° C.) δ: 10.38 (1H, s), 4.18 (2H, q, J=6.7 Hz), 3.07 (1H, d, J=18.0 Hz), 2.57 (1H, d, J=17.6 Hz), 1.22 (3H, t, J=7.2 Hz). $^{13}$C NMR (100 MHz, THF-d$_8$, 25° C.) δ: 177.6, 175.6, 171.8, 65.5, 62.8, 43.9, 14.4.

Example 3

Preparation of ethyl 3-hydrazino-2,5-dioxopyrrolidine-3-carboxylate

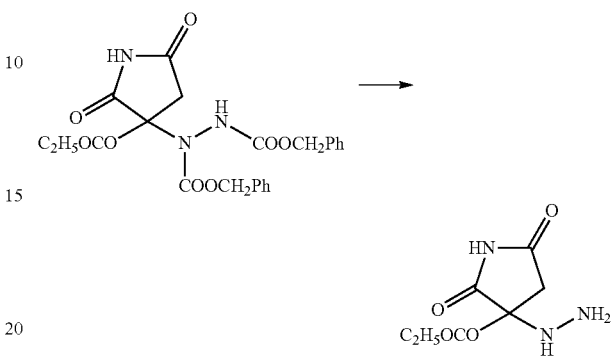

To a solution of the compound of Example 1 (1.00 g) in ethanol (30 ml) was added 5% palladium-carbon ethylenediamine complex (100 mg). The mixture was stirred vigorously at room temperature under hydrogen (atmospheric pressure) for 2.5 hours. During this reaction, to remove carbon dioxide generated with the progress of the reaction, the gas in the reactor was replaced with hydrogen gas several times. The reaction mixture was filtered through a Celite pad and then the Celite was washed with ethanol. The filtrate combined with the washers was concentrated to give the desired product (432 mg, quantitative) as oil $^1$H NMR (300 MHz, DMSO-d$_6$, 25° C.) δ: 4.16 (2H, q, J=7.1 Hz), 2.96 (1H, d, J=17.8 Hz), 2.86 (1H; d, J=17.9 Hz), 1.18 (3H, t, J=7.1 Hz).

Example 4

Preparation of ethyl 3-[N, N'-bis(tert-butyloxycarbonyl)hydrazino]-2,5-dioxopyrrolidine-3-carboxylate

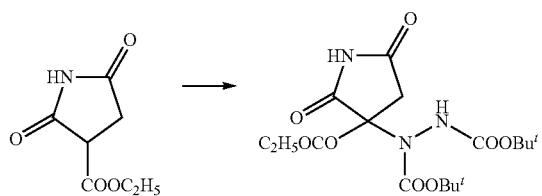

To a solution of ethyl 2,5-dioxopyrrolidine-3-carboxylate (2.96 g) in ethyl acetate (25 ml) was added di-tert-butyl azodicarboxylate (4.19 g), followed by potassium carbonate (4.78 g) at room temperature. After this reaction mixture was stirred at room temperature for 15 minutes, the resulting mixture was filtered through a Celite pad and the filtrate was concentrated. The residue was purified by a flash column chromatography (hexane:ethyl acetate=3:1) to give the desired product (5.77 g, 83%) as amorphous.

$^1$H NMR (300 MHz, DMSO-d$_6$, 120° C.) δ: 11.3 (1H, br), 8.80 (1H, br), 4.20 (2H, q, J=7.1 Hz), 3.41 (1H, d, J=18.1 Hz), 3.17 (1H, d, J=18.1 Hz), 1.41 (9H, s), 1.40 (9H, s), 1.23 (3H, t, J=7.1 Hz).

Example 5

Preparation of ethyl 3-hydrazino-2,5-dioxopyrrolidine-3-carboxylate monohydrochloride

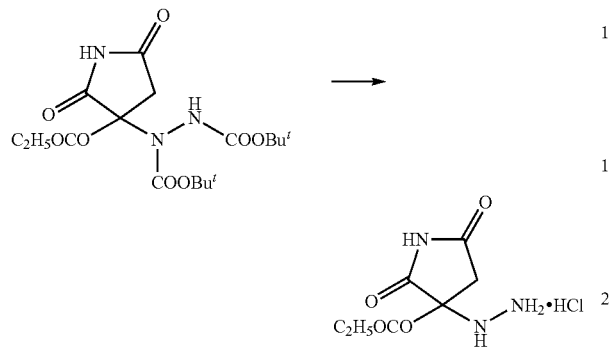

To a solution of the compound of Example 4 (5.77 g) in ethyl acetate (20 ml) was added a solution of 4M hydrogen chloride in ethyl acetate (25 ml) and the mixture was stirred at room temperature for 24 hours. The resulting precipitates were collected by filtering and washed with ethyl acetate to give the desired product (3.02 g, 76%) as powder. The desired product was identified to be a monohydrochloride salt thereof by the results of elementary analysis and X-ray crystallographic analysis. Melting point: 189-190° C. (decomposition). $^1$H NMR (300 MHz, DMSO-$d_6$, 25° C.) δ: 12.1 (1H, br), 9.58 (3H, br), 4.23 (2H, q, J=7.0 Hz), 3.15 (2H, s), 1.22 (3H, t, J=7.1 Hz). Elementary analysis: Calculated for $C_7H_{12}ClN_3O_4$: C, 35.38; H, 5.09; Cl, 14.92; N, 17.68. Founded: C, 35.28; H, 5.02; Cl, 14.83; N, 17.68.

Example 6

Preparation of ethyl 3-amino-2,5-dioxopyrrolidine-3-carboxylate

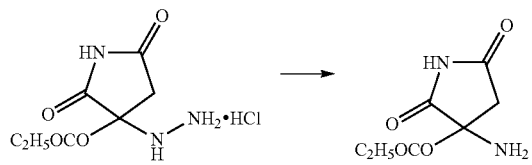

To a mixture of the compound of Example 5 (274 mg), acetic acid (10 ml) and water (5 ml) was added platinum oxide (25.5 mg) and the mixture was stirred vigorously at 50° C. under hydrogen (atmospheric pressure) for 6 hours. The reaction mixture was filtered through a Celite pad and the Celite was washed with a small amount of acetic acid. To the mixture of the filtrate combined with the washers was added sodium acetate (164 mg) and the mixture was concentrated. To the residue was added toluene to remove azeotropically the residual acetic acid and water and then the mixture was concentrated again. To the residue was added ethyl acetate and the insoluble product was filtered off, and then the ethyl acetate solution was concentrated to give the crude product and it was purified by a flash column chromatography (chloroform:methanol=30:1) to give the desired product (122 mg, 66%) as crystal.

Example 7

Preparation of ethyl 3-amino-2,5-dioxopyrrolidine-3-carboxylate

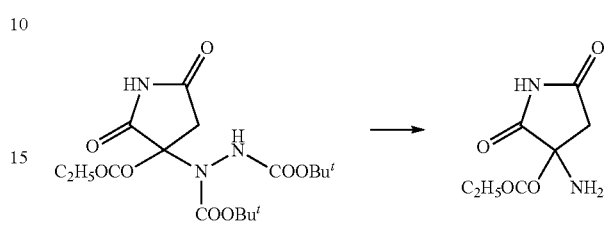

To a solution of the compound of Example 4 (970 mg) in dichloromethane (8 ml) was added trifluoroacetic acid (4 ml) and the mixture was stirred at room temperature for 6 hours. The reaction mixture was concentrated and to the resulting residue was added toluene to remove azeotropically the residual trifluoroacetic acid and then the mixture was concentrated again. The residue was dissolved in ethanol (25 ml) and thereto was added an appropriate amount of Raney nickel. This mixture was stirred vigorously at 40° C. under hydrogen (atmospheric pressure) for 24 hours. To the reaction mixture was added water (20 ml) and the mixture was filtered through a Celite pad and then the Celite was washed with ethanol. The mixture of the filtrate combined with the washers was adjusted to pH 7-8 with sodium bicarbonate and then thereto was added pH 7.4 phosphate buffer solution. This mixture was extracted with ethyl acetate and the extract was dried over magnesium sulfate and filtered. The filtrate was concentrated to give an oil which was then purified by a flash column chromatography (chloroform:methanol=20:1→10:1) to give the desired product (292 mg, 65%) as crystal.

Example 8

Preparation of (S)-(+)-camphorsulfonic acid salt of ethyl (R)-3-amino-2,5-dioxopyrrolidine-3-carboxylate Ethyl 3-amino-2,5-dioxopyrrolidine-3-carboxylate (8.00 g) and (S)-(+)-camphorsulfonic acid (10.0 g) were dissolved in ethanol (80 ml) while warming, and this solution was concentrated under reduced pressure to about 45 ml in total. This solution was allowed to stand under ice-cooling and precipitated crystal was collected by filtering and washed with ethanol. This crystal was recrystallized from ethanol to give the desired product (4.70 g) as crystal.

Melting point: 229-230° C. (decomposition). $[\alpha]_D^{27}$+10.2° (c 1.03, MeOH).

$^1$H NMR (400 MHz, $D_2O$, 23° C.) δ: 4.43 (2H, q, J=7.2 Hz), 3.56 (1H, d, J=18.8 Hz), 3.28 (1H, d, J=15.2 Hz), 3.22 (1H, d, J=18.8 Hz), 2.86 (1H, d, J=14.8 Hz), 2.46-2.37 (1H, m), 2.16 (1H, t, J=4.8 Hz), 2.09-2.00 (1H, m), 1.84 (1H, d, J=18.8 Hz), 1.68-1.61 (1H, m), 1.49-1.42 (1H, m), 1.30 (3H, t, J=7.2 Hz), 1.04 (3H, s), 0.83 (3H, s).

Example 9

Preparation of (S)-(+)-camphorsulfonic acid salt of ethyl (R)-3-amino-2,5-dioxopyrrolidine-3-carboxylate To a solution of the compound of Example 1 (2.04 g) in acetic acid (30 ml) was added platinum oxide (393 mg) and the mixture was stirred vigorously at 50° C. under hydrogen (atmospheric pressure) for 8 hours. During this reaction, to remove carbon dioxide generated with the progress of the reaction, the gas in the reactor was replaced with hydrogen gas several times. The reaction mixture was filtered through a Celite pad and then the Celite was washed with a small amount of acetic acid. The filtrate combined with the washers was concentrated and to the resulting residue was added toluene to remove azeotropically the residual acetic acid and then the mixture was concentrated again. To the residue was added ethyl acetate and the insoluble product was filtered off and then the ethyl acetate solution was concentrated to give the crude product (918 mg). The crude product and (S)-(+)-camphorsulfonic acid (1.09 g) were dissolved in ethanol (40 ml) while warming and this solution was concentrated under reduced pressure to 4-5 ml in total. This resulting mixture was allowed to stand at room temperature and the precipitated crystal was collected by filtering and washed with ethanol to give the desired product (356 mg, 20%) as crystal.

Example 10

Preparation of ethyl (R)-2,5-dioxo-3-(pyrrol-1-yl) pyrrolidine-3-carboxylate (S)-(+)-Camphorsulfonic acid salt of ethyl (R)-3-amino-2,5-dioxopyrrolidine-3-carboxylate (418 mg) was dissolved in 25% aqueous acetic acid solution (4 ml). Thereto were added sodium acetate (82 mg) and 2,5-dimethoxytetrahydrofuran (0.143 ml) and the mixture was stirred at 70° C. for 1.5 hours. After allowed to cool, to this mixture was added ethyl acetate (20 ml) and then the mixture were washed with water, followed by saturated brine and dried over magnesium sulfate and filtered. The filtrate was concentrated to give an oil. This was purified by a flash column chromatography (hexane:ethyl acetate=3:1) to give the desired product (230 mg, 97%) as oil. $^1$H NMR (CDCl$_3$) data were consistent with those described in J. Med. Chem., 1998, 41, p. 4118 to 4129.

$^1$H NMR (400 MHz, CDCl$_3$, 23° C.) δ: 9.05 (1H, br), 6.94 (2H, t, J=2.2 Hz), 6.26 (2H, t, J=2.2 Hz), 4.28 (2H, q, J=7.2 Hz), 3.59 (1H, d, J=17.6 Hz), 3.36 (1H, d, J=18.0 Hz), 1.26 (3H, t, J=7.2 Hz). $^{13}$C NMR (100 MHz, CDCl$_3$, 24° C.) δ: 172.7, 170.5, 166.8, 120.0, 110.1, 68.6, 63.9, 41.9, 13.8. MS (APCI): 237(M+H).

Ethyl (R)-2,5-dioxo-3-(pyrrol-1-yl)pyrrolidine-3-carboxylate (220 mg) was dissolved in ethyl acetate (1 ml) and thereto was added diisopropylamine (0.130 ml). To this solution was added hexane (1 ml) and the resulting white suspension was warmed at 40° C. to give a homogeneous solution. This mixture was allowed to stand at room temperature and precipitated crystal was collected by filtering to give ethyl (R)-2,5-dioxo-3-(pyrrol-1-yl)pyrrolidine-3-carboxylate diisopropylamine salt (198 mg, 60%) as crystal.

Melting point: 80-85° C. $^1$H NMR (400 MHz, DMSO-d$_6$, 22° C.) δ: 6.96 (2H, t, J=2.4 Hz), 6.01 (2H, t, J=2.2 Hz), 4.14-4.07 (2H, m), 3.27 (1H, d, J=17.2 Hz), 3.24-3.18 (2H, m), 2.98 (1H, d, J=17.2 Hz), 1.14 (12H, d, J=6.4 Hz), 1.13 (3H, t, J=6.8 Hz).

Example 11

Preparation of (3R)-2'-(4-bromo-2-fluorobenzyl) spiro[pyrrolidine-3,4'(1'H)-pyrrolo[1,2-a]pyr azine]-1',2,3',5(2H')-tetraone (1) To a solution of ethyl (R)-2,5-dioxo-3-(pyrrol-1-yl)pyrrolidine-3-carboxylate (767 mg) in ethyl acetate (10 ml) was added trichloroacetyl chloride (1.1 ml) and this solution was heated under reflux overnight. This reaction mixture was allowed to cool to room temperature, and thereto was added trichloroacetyl chloride (1.1 ml) and this mixture was heated under reflux for 3 hours. This reaction mixture was allowed to water-cooling to room temperature and the residual trichloroacetyl chloride was decomposed carefully with saturated aqueous sodium bicarbonate solution. After the aqueous layer was confirmed to be alkali, this mixture was extracted with ethyl acetate (5 ml) three times and the combined extract was washed with water and saturated brine successively, dried over magnesium sulfate, filtered and then concentrated to give a crude product as oil. This was purified by a flash column chromatography (n-hexane:ethyl acetate=1:1) to give ethyl (R)-2,5-dioxo-3-(2-trichloroacetylpyrrol-1-yl)pyrrolidine-3-carboxylate (1.17 g, 94%).

$^1$H NMR (400 MHz, DMSO-d$_6$, 22° C.) δ: 12.4 (br s, 1H), 7.68 (dd, 1H, J=1.2, 4.4 Hz), 7.55 (dd, 1H, J=1.6, 2.8 Hz), 6.44 (dd, 1H, J=2.4, 4.4 Hz), 4.25-4.08 (m, 2H), 3.72 (d, 1H, J=18.0 Hz), 3.06 (d, 1H, J=18.0 Hz), 1.11 (t, 3H, 7.2 Hz).

(2) To a solution of 4-bromo-2-fluorobenzylamine (0.93 g) and triethylamine (1.3 ml) in N,N-dimethylformamide (5 ml) was added a solution of ethyl (R)-2,5-dioxo-3-(2-trichloroacetylpyrrol-1-yl)pyrrolidine-3-carboxylate (1.16 g) in N,N-dimethylformamide (3 ml) dropwise at room temperature. This mixture was stirred at room temperature for 8 hours. This reaction mixture was diluted with ethyl acetate, then washed with 1M hydrochloric acid (three times), water (four times), and saturated brine successively, dried over magnesium sulfate, filtered and concentrated to give a crude product as yellow oil. This was purified by flash column chromatography (n-hexane:ethyl acetate=2:1) to give (3R)-2'-(4-bromo-2-fluorobenzyl)spiro [pyrrolidine-3,4'(1'H)-pyrrolo[1,2-a]pyr azine]-1',2,3',5 (2H')-tetraone (831 mg, 65%). This product was further crystallized from n-hexane-ethyl acetate to give the desired product (385 mg) as crystal.

Mp: 189-191° C. $^1$H NMR (400 MHz, DMSO-d$_6$, 22° C.) δ: 12.2 (br s, 1H), 7.73 (dd, 1H, J=2.0, 3.2 Hz), 7.55 (dd, 1H, J=2.0, 9.6 Hz), 7.36 (dd, 1H, J=2.0, 8.4 Hz), 7.17-7.12 (m, 2H), 6.53 (dd, 1H, J=2.8, 4.0 Hz), 5.04 (d, 1H, J=15.2 Hz), 4.96 (d, 1H, J=15.6 Hz), 3.57 (s, 2H).

Industrial Applicability

The present compound can be prepared in two or three steps from diethyl malonate as a starting material, and further it can be converted into the compound of the formula (IV) as being a key intermediate of tetrahydropyrrolo[1,2-a]pyrazin-4-spiro-3'-pyrrolidine derivatives in one step. Additionally, the manufacturing process of the present invention does not require the use of hydrogen peroxide and also the yield of each step is high. Thus the compounds of the present invention are useful as an intermediate of tetrahydropyrrolo[1,2-a] pyrazin-4-spiro-3'-pyrrolidine derivatives such as Ranirestat being useful as a therapeutic agent for diabetic complications.

The invention claimed is:

1. A process for preparing 2'-(4-bromo-2-fluorobenzyl) spiro[pyrrolidine-3,4'(1'H)-pyrrolo[1,2-a]pyrazine]-1',2,3',5 (2H')-tetraone, comprising the following steps:

(1) converting a compound of formula (Ia) into a compound of formula (IV):

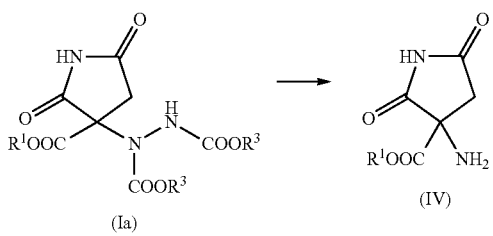

(Ia)                                    (IV)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group; or an aryl group or a heteroaryl group optionally substituted by one or two groups independently selected from the group consisting of a $C_{1-4}$ alkyl group, and a $C_{1-4}$ alkoxy group;

$R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group, with the proviso that the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group is excluded, or a 2,2,2-trichloroethyl group, by decomposing the compound of formula (Ia) wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group in a catalytic hydrogenolysis or a catalytic hydrogen transfer, or by reacting the compound of formula (Ia) wherein $R^3$ is a 2,2,2-trichloroethyl group with zinc;

(2) converting an amino group of the compound of formula (IV) of step (1) into a 1-pyrrolyl group;

(3) converting the 1-pyrrolyl group of step (2) into a 2-trichloroacetylpyrrol-1-yl group; and (4) reacting a product of step (3) with 4-bromo-2-fluorobenzylamine to convert the product of step (3) into 2'-(4-bromo-2-fluorobenzyl)spiro[pyrrolidine-3,4'(1'H)-pyrrolo[1,2-a]pyrazine]-1'2,3'5(2H')-tetraone.

2. The process according to claim 1, wherein the process comprises a step of preparing the compound of formula (Ia) by reacting the compound of formula (II):

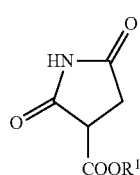

(II)

wherein $R^1$ is as defined in claim 1, with a compound of formula (III):

$R^3OOC-N=N-COOR^3$ (III)

wherein $R^3$ is as defined in claim 1, in the presence or absence of a base.

3. A process for preparing (3R)-2'-(4-bromo-2-fluorobenzyl)spiro[pyrrolidine-3,4'(1'H)-pyrrolo[1,2-a]pyrazine]-1',2,3',5(2H')-tetraone, comprising the following steps:

(1) converting a compound of formula (Ia) into a compound of formula (IV):

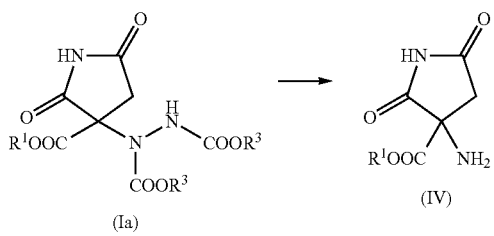

(Ia)                                    (IV)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group; or an aryl group or a heteroaryl group optionally substituted by one or two groups independently selected from the group consisting of a $C_{1-4}$ alkyl group, and a $C_{1-4}$ alkoxy group;

$R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group, with the proviso that the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group is excluded, or a 2,2,2-trichloroethyl group, by decomposing the compound of formula (Ia) wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group in a catalytic hydrogenolysis or a catalytic hydrogen transfer, or by reacting the compound of formula (Ia) wherein $R^3$ is a 2,2,2-trichloroethyl group with zinc;

(2) performing an optical resolution of the compound of formula (IV) of step (1);

(3) converting an amino group of the optically active compound of step (2), wherein the absolute configuration at the carbon atom on the 3 position of the dioxopyrrolidine ring of the optically active compound of step (2) is R, into a 1-pyrrolyl group;

(4) converting the 1-pyrrolyl group of step (3) into a 2-trichloroacetylpyrrol-1-yl group; and (5) reacting a product of step (4) with 4-bromo-2-fluorobenzylamine to convert the product of step (4) into (3R)-2'-(4-bromo-2-fluorobenzyl)spiro[pyrrolidine-3,4'(1'H)-pyrrolo[1,2-a]pyrazine]-1',2,3',5(2H')-tetraone.

4. The process according to claim 3, wherein $R^1$ is a $C_{1-6}$ alkyl group other than a tert-$C_{4-6}$ alkyl group, and $R^3$ is a tert-$C_{4-6}$ alkyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group.

5. The process according to claim 3, wherein $R^1$ is a methyl group, an ethyl group, a propyl group or an isopropyl group, and $R^3$ is a tert-butyl group or a benzyl group.

6. The process according to claim 3, wherein the compound of formula (Ia) is selected from the group consisting of
ethyl 3-[N,N'-bis(benzyloxycarbonyl)hydrazino]-2,5-dioxopyrrolidine-3-carboxylate, and
ethyl 3-[N,N'-bis(tert-butoxycarbonyl)hydrazino]-2,5-dioxopyrrolidine-3-carboxylate.

7. The process according to claim 3,
wherein the process comprises a step of preparing the compound of formula (Ia) by reacting the compound of formula (II):

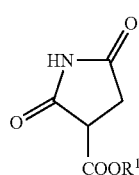

(II)

wherein $R^1$ is as defined in claim 3, with a compound of formula (III):

(III)

wherein $R^3$ is as defined in claim 3, in the presence or absence of a base.

8. The process according to claim 7, wherein the compound of formula (Ia) is a compound wherein $R^1$ is a $C_{1-6}$ alkyl group other than a tert-$C_{4-6}$ alkyl group, and $R^3$ is a tert-$C_{4-6}$ alkyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group.

9. The process according to claim 7, wherein the compound of formula (Ia) is a compound wherein $R^1$ is a methyl group, an ethyl group, a propyl group or an isopropyl group, and $R^3$ is a tert-butyl group or a benzyl group.

10. The process according to claim 7, wherein the compound of formula (Ia) is selected from the group consisting of
ethyl 3-[N,N'-bis(benzyloxycarbonyl)hydrazino]-2,5-dioxopyrrolidine-3-carboxylate, and
ethyl 3-[N,N'-bis(tert-butoxycarbonyl)hydrazino]-2,5-dioxopyrrolidine-3-carboxylate.

11. A process for preparing 2'-(4-bromo-2-fluorobenzyl) spiro[pyrrolidine-3,4'(1'H)-pyrrolo[1,2-a]pyrazine]-1',2,3',5 (2'H)-tetraone, comprising the following steps:
(1) converting a compound of formula (Ia) into a compound of formula (Ib):

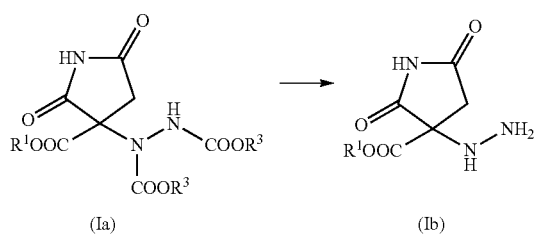

(Ia)                (Ib)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group; or an aryl group or a heteroaryl group optionally substituted by one or two groups independently selected from the group consisting of a $C_{1-4}$ alkyl group, and a $C_{1-4}$ alkoxy group;

when $R^1$ is a $C_{1-6}$ alkyl group other than a tert-$C_{4-6}$ alkyl group; a $C_{3-8}$ cycloalkyl group; or an aryl group or a heteroaryl group optionally substituted by one or two groups independently selected from the group consisting of a $C_{1-4}$ alkyl group and a $C_{1-4}$ alkoxy group, then $R^3$ is a tert-$C_{4-6}$ alkyl group; a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group;

when $R^1$ is a tert-$C_{4-6}$ alkyl group, then $R^3$ is a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group;

when $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group, then $R^3$ is a tert-$C_{4-6}$ alkyl group or a 2,2,2-trichloroethyl group, by reacting the compound of formula (Ia) wherein $R^3$ is a tert-$C_{4-6}$ alkyl group with an acid, by reacting the compound of formula (Ia) wherein $R^3$ is a 2,2,2-trichloroethyl group with zinc, or by undergoing a hydrogenolysis of the compound of formula (Ia) wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group in the presence of a catalyst;

(2) converting the compound of formula (Ib) of step (1) into the compound of formula (IV)

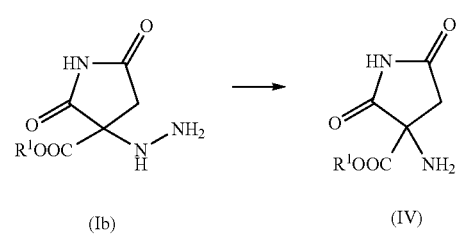

(Ib)                (IV)

by decomposing the compound of formula (Ib) in a catalytic hydrogenolysis or a catalytic hydrogen transfer, with the proviso that the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group is excluded, or reacting the compound of formula (Ib) with zinc;

(3) converting an amino group of the compound of formula (IV) of step (2) into a 1-pyrrolyl group;

(4) converting the 1-pyrrolyl group of step (3) into a 2-trichloroacetylpyrrol-1-yl group; and (5) reacting the product of step (4) with 4-bromo-2-fluorobenzylamine to convert the product of step (4) into 2'-(4-bromo-2-fluorobenzyl)spiro[pyrrolidine-3 ,4'(1'H)-pyrrolo[1,2-a]pyrazine]-1',2,3',5(2H')-tetraone.

12. The process according to claim 11,
wherein the process comprises a step of preparing the compound of formula (Ia) by reacting a compound of formula (II):

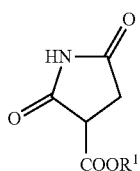

(II)

wherein $R^1$ is as defined in claim 11, with a compound of formula (III):

$R^3OOC—N=N—COOR^3$ (III)

wherein $R^3$ is as defined in claim 11, in the presence or absence of a base.

13. A process for preparing (3R)-2'-(4-bromo-2-fluorobenzyl)spiro[pyrrolidine-3,4'(1 'H)-pyrrolo[1,2-a]pyrazine]-1',2,3',5(2H')-tetraone, comprising the following steps:
(1) converting a compound of formula (Ia) into a compound of formula (Ib):

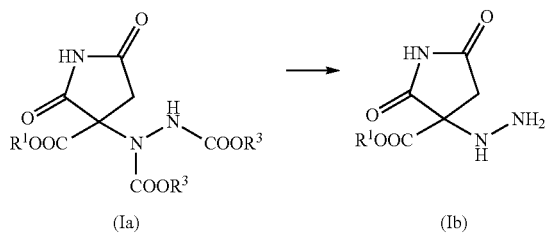

(Ia)         (Ib)

wherein $R^1$ is a $C_{1-6}$ alkyl group; a $C_{3-8}$ cycloalkyl group; a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group; or an aryl group or a heteroaryl group optionally substituted by one or two groups independently selected from the group consisting of a $C_{1-4}$ alkyl group, and a $C_{1-4}$ alkoxy group;
when $R^1$ is a $C_{1-6}$ alkyl group other than a tert-$C_{4-6}$ alkyl group; a $C_{3-8}$ cycloalkyl group;
or an aryl group or a heteroaryl group optionally substituted by one or two groups independently selected from the group consisting of a $C_{1-4}$ alkyl group and a $C_{1-4}$ alkoxy group, then $R^3$ is a tert-$C_{4-6}$ alkyl group; a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group;
when $R^1$ is a tert-$C_{4-6}$ alkyl group, then $R^3$ is a 2,2,2-trichloroethyl group; or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group;

when $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, and a cyano group, then $R^3$ is a tert-$C_{4-6}$ alkyl group or a 2,2,2-trichloroethyl group,
by reacting the compound of formula (Ia) wherein $R^3$ is a tert-$C_{4-6}$ alkyl group with an acid,
by reacting the compound of formula (Ia) wherein $R^3$ is a 2,2,2-trichloroethyl group with zinc, or
by undergoing a hydrogenolysis of the compound of formula (Ia) wherein $R^3$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group in the presence of a catalyst;
(2) converting the compound of formula (Ib) of step (1) into the compound of formula (IV)

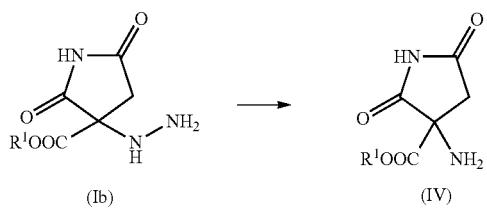

(Ib)         (IV)

by decomposing the compound of formula (Ib) in a catalytic hydrogenolysis or a catalytic hydrogen transfer, with the proviso that the compound wherein $R^1$ is a benzyl group in which the benzene ring moiety may be optionally substituted by one or two atoms or groups independently selected from the group consisting of a halogen atom, a $C_{1-4}$ alkyl group, a $C_{1-4}$ alkoxy group and a cyano group is excluded, or reacting the compound of formula (Ib) with zinc;
(3) performing an optical resolution of the compound of formula (IV) of step (2);
(4) converting an amino group of the optically active compound of step (3), wherein the absolute configuration at the carbon atom on the 3 position of the dioxopyrrolidine ring of the optically active compound of step (3) is R, into a 1-pyrrolyl group;
(5) converting the 1-pyrrolyl group of step (4) into a 2-trichloroacetylpyrrol-1-yl group; and
(6) reacting a product of step (5) with 4-bromo-2-fluorobenzylamine to convert the product of step (5) into (3R)-2'-(4-bromo-2-fluorobenzyl)spiro[pyrrolidine-3,4'(1'H)-pyrrolo[1,2-a]pyrazine]-1',2,3',5(2H')-tetraone.

14. The process according to claim 13, wherein $R^1$ is a $C_{1-6}$ alkyl group other than a tert-$C_{4-6}$ alkyl group, and $R^3$ is a tert-$C_{4-6}$ alkyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group.

15. The process according to claim 13, wherein $R^1$ is a methyl group, an ethyl group, a propyl group or an isopropyl group, and $R^3$ is a tert-butyl group or a benzyl group.

16. The process according to claim 13, wherein the compound of formula (Ia) is selected from the group consisting of
ethyl 3-[N,N'-bis(benzyloxycarbonyl)hydrazine]-2,5-dioxopyrrolidine-3 - carboxylate, and
ethyl 3-[N,N'-bis(tert-butoxycarbonyl)hydrazine]-2,5-dioxopyrrolidine-3 -carboxylate.

17. The process according to claim 13,
wherein the process comprises a step of preparing the compound of formula (Ia) by reacting a compound of formula (II):

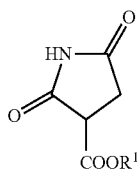  (II)

wherein $R^1$ is as defined in claim 13, with a compound of formula (III):

  (III)

wherein $R^3$ is as defined in claim 13, in the presence or absence of a base.

18. The process according to claim 17, wherein the compound of formula (Ia) is a compound wherein $R^1$ is a $C_{1-6}$ alkyl group other than a tert-$C_{4-6}$ alkyl group, and $R^3$ is a tert-$C_{4-6}$ alkyl group or a benzyl group in which the benzene ring moiety may be optionally substituted by one or two atoms or groups independently selected from the group consisting of a halogen atom, a $C_{1-4}$ alkyl group, a $C_{1-4}$ alkoxy group, a cyano group, and a nitro group.

19. The process according to claim 17, wherein the compound of formula (Ia) is a compound wherein $R^1$ is a methyl group, an ethyl group, a propyl group or an isopropyl group, and $R^3$ is a tert-butyl group or a benzyl group.

20. The process according to claim 17, wherein the compound of formula (Ia) is selected from the group consisting of
ethyl 3-[N,N'-bis(benzyloxycarbonyl)hydrazino]-2,5-dioxopyrrolidine-3-carboxylate, and
ethyl 3-[N,N'-bis(tert-butoxycarbonyl)hydrazino]-2,5-dioxopyrrolidine-3-carboxylate.

* * * * *